United States Patent [19]

Henry

[11] 4,200,753

[45] Apr. 29, 1980

[54] WATER-SOLUBLE FLUORESCING AND LASING DYES

[75] Inventor: Ronald A. Henry, China Lake, Calif.

[73] Assignee: The United States of America as represented by the Secretary of the Navy, Washington, D.C.

[21] Appl. No.: 961,578

[22] Filed: Nov. 17, 1978

[51] Int. Cl.² ............... C07D 491/04; C07D 311/16
[52] U.S. Cl. ............... 546/116; 260/343.43; 331/94.5 L
[58] Field of Search ............... 546/116; 260/343.43, 260/343.44, 343.45

[56] References Cited
U.S. PATENT DOCUMENTS

| | | |
|---|---|---|
| Re. 23,703 | 9/1953 | Ackermann ............... 260/343.43 |
| 3,927,033 | 12/1975 | Hammond ............... 260/343.44 |
| 4,103,256 | 7/1978 | Hammond et al. ............... 546/116 |

Primary Examiner—Alan L. Rotman
Assistant Examiner—Natalia Harkaway
Attorney, Agent, or Firm—R. S. Sciascia; W. Thom Skeer; L. E. K. Pohl

[57] ABSTRACT

Compounds having the structures:

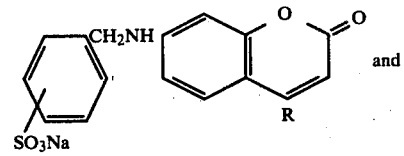

and

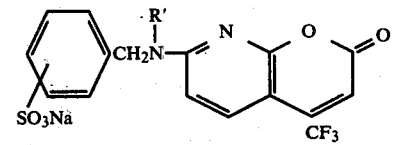

wherein R is $CH_3$ or $CF_3$ and wherein $R^1$ is H or $CH_3$. The compounds are prepared by a four step method involving (1) the formation of a benzylaminophenol or benzylaminohydroxypyridine, (2) the formation of a coumarin or azacoumarin, (3) sulfonation of the coumarin or azacoumarin and (4) neutralization of the sulfonate with sodium bicarbonate. The compounds are useful as water-soluble lasing dyes.

2 Claims, No Drawings

WATER-SOLUBLE FLUORESCING AND LASING DYES

BACKGROUND OF THE INVENTION

1. Field of the Invention

This invention relates to water-soluble lasing dyes.

2. Description of the Prior Art

When dyes are used in lasers, they are usually dissolved in organic solvents. One widely used solvent is ethanol.

As a solvent, water offers advantages over organic compounds in that it is more readily available, less expensive, non-toxic and non-flammable. Additionally, water has a higher boiling point and greater heat capacity than do most commonly used organic solvents. Accordingly, considerable interest in the preparation of water-soluble laser dyes has developed.

SUMMARY OF THE INVENTION

According to this invention, water-soluble coumarins and azacoumarins having the structures:

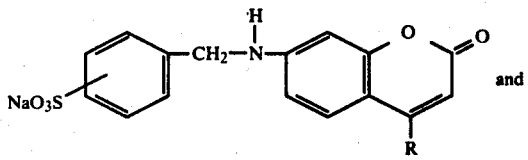

and

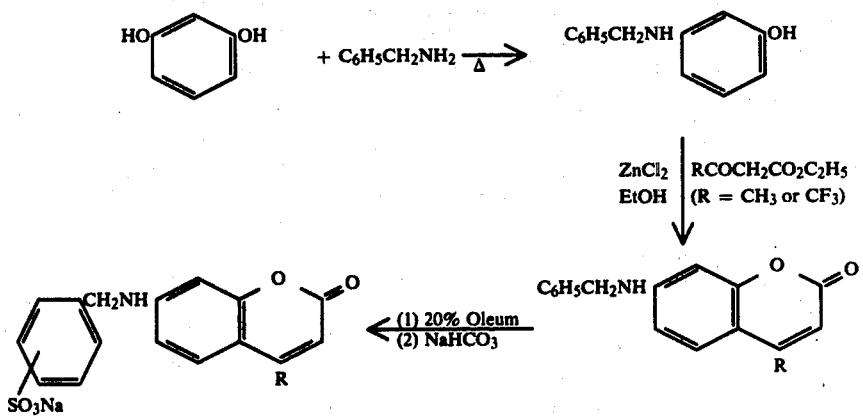

wherein R is $CH_3$ or $CF_3$ and wherein $R^1$ is H or $CH_3$ are prepared. The coumarins are prepared by means of a three step process involving (1) heating resorcinol and benzylamine to form 3-benzylaminophenol, (2) reacting the 3-benzylaminophenol with ethyl acetoacetate or ethyl trifluoroacetoacetate in the presence of anhydrous zinc chloride and absolute ethanol to form 7-benzylamino-4-methylcoumarin or 7-benzylamino-4-trifluoromethylcoumarin, (3) sulfonating the product of step (2) with oleum and (4) neutralizing the sulfonate formed in step (3) with sodium bicarbonate. The azacoumarins are prepared by a similar process except that 6-chloro-2-pyridinol and either benzylamine or benzylmethylamine are used as the starting compounds (the step (1) reactants).

DESCRIPTION OF THE PREFERRED EMBODIMENTS

The methods utilized in practicing this invention may be conveniently illustrated by means of the following schemes. Scheme 1 is used to produce the coumarins of this invention and scheme 2 is used to produce the azacoumarins.

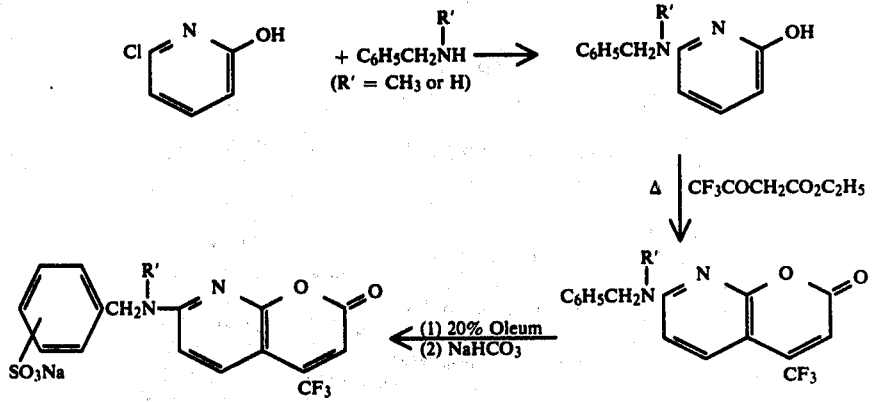

the steps of Scheme 1.

EXAMPLE 1

3-Benzylaminophenol. Resorcinol (22 g) and 21.4 g of benzylamine were heated under an air condenser in a nitrogen atmosphere at 175°–185° C. for 5.5 hr. Then the air condenser was removed, and the temperature raised to 200°–203° where it was held for 1.5 hr. The red, viscous mass was cooled and boiled with 250 ml of 3:2 benzene-cyclohexane to form a solution. The solution was cooled several days at 5° C. to allow for the separation of oily material. The supernatant was decanted and evaporated to leave 12.0 g (30%) of paleorange, viscous liquid 3-benzylaminophenol which was used without further purification.

EXAMPLE 2

7-Benzylamino-4-methylcoumarin was synthesized from 3-benzylaminophenol and ethyl acetoacetate by the usual Peckmann reaction (anhydrous zinc chloride, absolute ethanol). Recrystallization from ethanol gave flat needles, m.p. 174.5°–175.5° C. The fluorescence maximum in water was 455 nm (excited 355 nm), in $10^{-2}$ N HCl 458 nm. $^1$H nmr (60 MHz, CDCl$_3$), δ2.36 (s, 3H, C—CH$_3$), 4.45 (d, 2H, —CH$_2$ NH—, J=∼5.5 Hz, collapses to a singlet when D$_2$O added), 4.7–5 (1H, NH), 6.03 (s, 1H, H$_3$), 6.57 (d, 1H H$_8$), 6.63 (dd, 1H, H$_6$, J$_{56}$=∼9 Hz, J$_{68}$=∼2 Hz), 7.45 (s, 5H, C$_6$H$_5$), 7.45 (d, 1H, H$_5$, J$_{56}$=∼9 Hz).

Anal. Calcd. for C$_{17}$H$_{15}$NO$_2$: C, 76.96; H, 5.70: N, 5.28. Found, C, 76.85; H, 5.68; N, 5.21.

EXAMPLE 3

7-Benzylamino-4-trifluoromethylcoumarin was prepared by a method similar to that of Example 2 except that ethyl trifluoroacetoacetate was used. Recrystallization from 60:40 cyclohexane-benzene gave bright yellow felted needles; m.p. 136°–137°. Fl(max) H$_2$O: 450 nm (excited 350 nm); $10^{-2}$ N HCl, 514 nm (excited 390 nm). $^1$H nmr (100 MHz, CDCl$_3$), δ4.24 (d, 2H, —CH$_2$NH—, collapses to a singlet when D$_2$O added), 4.8–5.1 (1H, NH), 6.34 (s, 1H, H$_3$), 6.45 (d, 1H, H$_8$, J$_{68}$=2.3 Hz), 6.57 (dd, 1H, H$_6$, J$_{56}$=8.8 Hz, J$_{68}$=2.3 Hz), 7.36 (s, 5H, C$_6$H$_5$), 7.43 (doublet of quartets, 1H, H$_5$, J$_{56}$=8.8 Hz, J$_{5\text{-}CF_3}$=1.8 Hz).

Anal. Calcd. for C$_{17}$H$_{12}$F$_3$NO$_2$: N, 4.39. Found N, 4.34.

EXAMPLE 4

Sodium salt of 7-(3-Sulfobenzylamino)-4-methylcoumarin: 7-Benzylamino-4-methylcoumarin (0.9 g) was added over a period of 1 hour to 5 ml of 20% oleum with stirring and cooling in an ice-water bath. After 4 hours of stirring at 25° C., the acid was poured over 20 g of ice; the purple solid which crystallized was filtered off and washed once with a small volume of water (0.5 g; m.p. 225°–235°). When purified by fractional precipitation with ether from 60 ml of ethanol, an off-white solid was obtained, m.p. 300°. Fl(max), H$_2$O: 454 nm (excited 355).

Anal. Calcd. for C$_{17}$H$_{15}$NO$_5$S: N, 4.06; S, 9.28. Found: N, 4.24; S, 9.50.

The washings and aqueous solution were neutralized with sodium bicarbonate, ether extracted to remove any unsulfonated material, then evaporated to dryness. The residual cake was extracted with one 50 ml and two 25 ml portions of boiling 95% ethanol; evaporations of the combined extracts left 0.85 g of gummy solid, which was redissolved in a small amount of ethanol, filtered from any organic salts, and fractionally precipitated by adding ether. The first crops of solid were dark pink or tan colored, the latter pale yellow. $^1$H nmr spectra on four fractions including first and last were identical. $^1$H nmr (100 MHz, D$_2$O), 1.88 (s, 3H, 4-CH$_3$). 4.25 (s, 2H, CH$_2$), 5.55 (s, 1H, H$_3$), 5.95 (d, 1H, H$_8$, J$_{68}$=2.2 Hz), 6.14 (dd, 1H, H$_6$, J$_{56}$=8.8 Hz, J$_{68}$=2.2 Hz), 6.62 (d, 1H, H$_5$, J$_{56}$=8.8 Hz), 7.3–8.0 (m, 4H, phenyl). All portions were readily soluble in water with a strong blue fluorescence. Fl(max), H$_2$O: 453 nm (excited 355 nm).

Anal. Calcd. for C$_{17}$H$_{14}$NO$_5$SNa: N, 3.81; S, 8.73. Found: N, 3.71; S, 8.73.

EXAMPLE 5

Sodium Salts of 7-(3- and 4-Sulfobenzylamino)-4-trifluoromethylcoumarin:

7-(Benzylamino)-4-trifluoromethylcoumarin (3.8 g) was sulfonated with 20 ml of 20% oleum, employing the procedure used in Example 4. After quenching on 80 g of ice, the solution was neutralized with good cooling; 25% aqueous sodium hydroxide was used to neutralize the bulk of the acid, then sodium bicarbonate to finish the operation. Upon standing overnight at room temperature, a yellow, flocculent solid separated; it was removed by filtration, washed once with just enough ice water to wet the cake thoroughly (filtrate and washings saved) and dried; 2.7 g were obtained. Recrystallization from 100 ml of 95% ethanol plus 6 ml of water gave flat needles, m.p. 268°–273° C. Fl(max), H$_2$O: 510 nm (excited 390 nm); 50% aqueous ethanol: 502 nm (390); 95% ethanol: 495 nm (390). $^1$H nmr spectrum, 100 MHz, obtained in D$_2$O, suggested a mixture of the meta- and para-sulfonates, with the former isomer the main component. There are two kinds of benzyl methylene protons: δ4.30 (major), δ4.23 (minor). The pattern and splitting of the stronger signals in the benzyl aromatic region (δ7.3–7.8) are those found with a meta-substituted phenyl ring, the most definitive absorption being a doublet at δ7.82, showing only meta-splitting (the proton between the two substituents). The aromatic protons of the para-substituted benzyl group are proportionately less intense; although some of the signals are partially submerged in the aromatic protons of other isomer, a doubled doublet is evident, showing both ortho- and meta-splitting (∼9 and ∼2 Hz, respectively). The chemical shifts and line splittings for the other aromatic protons in the molecule follow: δ6.20 (s, 1H, H$_3$), 6.26 (d, 1H, H$_8$, J$_{68}$=2 Hz), 6.43 (dd, 1H, H$_6$, J$_{56}$=8.5 Hz, J$_{68}$=∼2 Hz), 7.11 (doubled triplets, 1H, J$_{56}$=8.5 Hz, J$_{H5\text{-}CF_3}$=∼2 Hz).

Anal. Calcd. for C$_{17}$H$_{11}$F$_3$NO$_5$SNa.H$_2$O: C, 46.47; H, 2.98; F, 12.97; N, 3.19; S, 7.30; Na, 5.23. Found: C, 46.65; H, 2.91; F, 11.30, 11.57; N, 3.42; S, 7.50; Na 5.40.

The original aqueous mother liquors and washings were evaporated to a thick paste, boiled with 100 ml of absolute ethanol, and the precipitated salts filtered off. The latter were in turn extracted with two 50 ml portions of boiling 95% ethanol. The combined alcoholic extracts were evaporated to dryness; the residue was extracted with one 50 ml and two 25 ml portions of boiling 95% ethanol (insoluble material was discarded). The cooled alcoholic extracts were treated with 30 ml of ether, cooled to 5° C. for several days, filtered from amorphous orange-brown solid, and treated with a large excess of ether. The pale yellow solid, which gradually separated, was removed, washed well with ether and dried; 1.4 g were obtained. The fluorescence of this product in water was the same as the crop described above. The $^1$H nmr on this fraction, based on the relative peak heights of the two different benzyl methylene groups, suggested that it was much richer in the para-sulfonated isomer than the main crop of material described above.

Anal. Calcd. for $C_{17}H_{11}F_3NO_5SNa\cdot H_2O$: F, 12.97; N, 3.19; S, 7.30. Found: F, 13.22; N, 3.21; S, 7.23.

The following specific examples further illustrate the steps of Scheme 2.

EXAMPLE 6

6-Benzylamino-2-hydroxypyridine: 6-Chloro-2-pyridinol (6.1 g, 0.047 mole) and 10.1 g (0.094 mole) of benzylamine were mixed and heated in an oil bath at 120°–130° for 48 hours. The liquid mass gradually solidified. The cooled mixture was boiled with 100 ml of 50% aqueous ethanol and cooled to 25° C.; the supernatant was decanted from a gum (which was saved), cooled to 5° C., decanted from black tar, and diluted with 50 ml of water. A grey, granular solid, m.p. 158°–162° C., crystallized. An additional quantity of the same material was recovered as follows: The retained gum was digested with 50 ml of hot 95% ethanol until it was solid; the mixture was cooled to 5° C., the solid removed, and the filtrate diluted with water. The total yield of the title compound was 2.4 g (25%). Recrystallization from benzene-n-hexane raised the m.p. to 164°–165°. $^1$H nmr (CDCl$_3$+D$_2$O, 100 MHz), $\delta$4.28 (s, 2H, CH$_2$), 5.28 (d, 1H, H$_5$, J=8 Hz), 5.50 (d, 1H, H$_3$, J=9 Hz), 7.17 (t, 1H, H$_4$, J=8 Hz), 7.30 (s, 5H, C$_6$H$_5$).

Anal. Calcd. for $C_{12}H_{12}N_2O$: C, 71.97; H, 6.04; N, 13.99. Found: C, 72.33; H, 6.06; N, 13.61.

EXAMPLE 7

6-(Benzylmethyl)amino-2-hydroxypyridine: 6-Chloropyridinol-2 (12.0 g, 0.1 mole) and 24.2 g (0.2 mole) of benzylmethylamine were mixed, flushed with dry nitrogen for 0.5 hour, then heated for 24 hours under N$_2$ at 120°–130° C. Upon cooling the reaction mixture solidified to a pale yellow mass, which was next dissolved in 200 ml of boiling 50% aqueous ethanol, diluted with 25 ml of water, cooled to 5° C., filtered through Celite to remove tarry material, and seeded. After several days at 5° C. the product was removed, washed with cold aqueous ethanol and dried; 9.7 g (45%), m.p. 97°–99° C. An additional 1.0 g of less pure material was recovered by diluting the mother liquors with 100 ml of water. Recrystallization from cyclohexane furnished white blades, melting at 99°–100°. $^1$H nmr (CDCl$_3$, 60 MHz), $\delta$3.08 (s, 3H, CH$_3$), 4.67 (s, 2H, CH$_2$), 5.50 (d, 1H, H$_5$, J=~8 Hz), 5.86 (d, 1H, H$_3$, J=~8 Hz), 7.32 (s, 5H, C$_6$H$_5$), 7.32 (t, 1H, H$_4$, J=~8 Hz).

Anal. Calcd. for $C_{13}H_{14}N_2O$: C, 72.87; H, 6.59; N, 13.08. Found: C, 73.03; H, 6.84; N, 12.91.

EXAMPLE 8

7-(Benzylmethyl)amino-4-trifluoromethyl-8-azacoumarin:

(A) 6-Benzylmethyl)amino-2-hydroxypyridine (9.7 g) and 14 ml of ethyl trifluoroacetoacetate were heated under a water condenser at a pot temperature of 135°–140° C. for 18 hours. Then the water condenser was replaced by an air condenser and the temperature raised to 155°–160° C. for 5 hours. The cooled mixture, which partially crystallized, was stirred with 25 ml of cyclohexane; the solid was removed and washed once with a small quantity of clod cyclohexane. (The mother liquors and washings were saved.) The solid was dissolved in 100 ml of hot ethanol and the solution cooled to 5° C., the thick mass of off-white felted needles was filtered promptly and washed three times with cold ethanol; 8.7 g (78%), m.p. 120°–130° C. This fraction was mainly a 1:1 adduct of starting reactants. Further cooling of the alcoholic mother liquors at 5° C. yielded 2.3 g (15%) of the title compound, m.p. 104°–106° C.; an additional 1.0 g (7%) was recovered by seeding and cooling the retained cyclohexane solutions. Recrystallization from methanol or ethanol gave greenish yellow plates, m.p. 105°–106° C. Fluorescence (max): ethanol, 472 nm (excited 395 nm); 50% aqueous ethanol, 478 nm. $^1$H nmr (CDCl$_3$, 100 MHz), $\delta$3.19 (s, 3H, CH$_3$), 4.87 (s, 2H, CH$_2$), 6.45 (d, 1H, H$_3$, $J_{H3-CF3}$=0.6 Hz), 6.52 (d, 1H, H$_6$, J$_{56}$=9 Hz), 7.28 (s, 5H, C$_6$H$_5$), 7.74 (dq, 1H, H$_5$, J$_{56}$=9 Hz, $J_{H5-CF3}$=2 Hz).

Anal. Calcd. for $C_{17}H_{13}F_3N_2O_2$: C, 61.08; H, 3.92; F, 17.05; N, 8.38. Found: C, 61.02; H, 3.91; F, 17.43; N, 8.48, 8.06.

(B) One gram of the 1:1 adduct was heated in an oil bath at 158°–162° C. for 19 hours. The resulting dark, tarry resin was boiled with 10 ml of cyclohexane, cooled to ambient, and the supernatant decanted. This extraction process was repeated three times more. The combined extracts were seeded, allowed to stand several hours at 25°, then overnight at 5°; the yellow orange crusts were removed and washed with cold cyclohexane; 0.4 g (48%), m.p. 103°–105° C. The infrared spectrum was identical with that for the product from Example 8A.

EXAMPLE 9

7-Methylamino-4-trifluoromethyl-8-azacoumarin and the Sodium Salt of 7-[(3- and/or 4-sulfobenzyl)methyl]-4-trifluoromethyl-8-azacoumarin:

Three grams of the azacoumarin from Example 8 were added over 1 hour and 40 minutes to 22 ml of 20% oleum with good stirring and ice bath cooling. After the solution had been stirred for 4 hours at 25°, it was poured slowly over 50 g of ice (additional ice was added as needed) with good mixing. Ethanol (50 ml) was added and the solution then neutralized with sodium bicarbonate; more water was added to keep the sodium sulfate from crystallizing. The total volume of the solution after neutralization was about 400 ml. Some yellow insoluble material was removed, washed with water and dried; recrystallization from ethanol gave bright yellow needles, m.p. 223.5°–224.5° C., of 7-methylamino-4-trifluoromethyl-8-azacoumarin. Fluorescence (max.): 95% ethanol, 460 nm (excited 380 nm); 50% aqueous ethanol, 470 nm.

$^1$H nmr (CDCl$_3$+DMSO-d$_6$, 60 MHz), $\delta$2.90 (d, 3H, CH$_3$-NH, J=~4 Hz), 6.48 (s, 1H, H$_3$), 6.63 (d, 1H, H$_6$, J$_{56}$=8 Hz), 7.69 (dd, 1H, H$_5$, J$_{56}$=8 Hz, $J_{H5-CF3}$=2 Hz)

Anal. Calcd. for $C_{10}H_7F_3N_2O_2$: C, 49.19; H, 2.89; F, 23.34; N, 11.48. Found: C, 49.14; H, 2.78; F, 23.54; N, 11.39.

The aqueous mother liquors were concentrated on a rotary evaporator at room temperature to a thick paste, which was extracted with one 200 ml portion of boiling 90% ethanol and two 50 ml portions of boiling 85% ethanol. The combined, dark green extracts were taken to dryness, again on a rotary evaporator. This residue was extracted with one 100 ml and two 10 ml portions of boiling 85% ethanol; the cooled extracts were diluted with 25 ml of ether, chilled to 5°, decanted from a green resin, treated with 25 ml more of ether, quickly filtered from more resin, and allowed to stand at 25°. Rosettes of pale yellow, felted needles slowly crystallized. Further crops of material were obtained by cooling the mother liquors and by adding additional increments of ether. The early crops were either non-fluorescent or only weakly fluorescent in water, the latter more strongly fluorescent. Both the analyses and the $^1$H nmr suggest that the early crops were primarily the following compound:

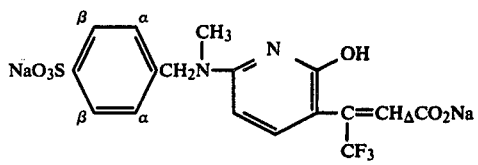

$^1$H nmr (D$_2$O, 60 MHz), $\delta$3.10 (s, 3H, CH$_3$), 4.74 (s, 2H, CH$_2$), 5.77 (d, 1H, H$_5$), 6.86 (q, 1H, H$_\Delta$, $J_{H\Delta-CF_3}$=1.5 Hz), 7.41 (d, 3H, H$_4$, H$_\alpha$, J=8.5 Hz), 7.87 (d, 2H, H$_\beta$, J=8.5 Hz).

Anal. Calcd. for C$_{17}$H$_{13}$F$_3$N$_2$O$_6$SNa$_2$.1 H$_2$O: N, 5.67; S, 6.49; Na, 9.30. Found: N, 5.63; S, 6.60; Na, 9.55.

The next crops contained the following compound:
Fl (max); H$_2$O, 477 nm (excited 390 nm); 50% aqueous ethanol, 475 nm

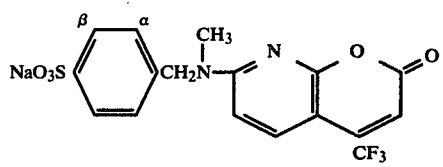

$^1$H nmr (DMSO-d$_6$, 60 MHz), $\delta$2.93 (s, 3H, CH$_3$), 4.70 (s, 2H, CH$_2$)., 6.02 (d, 1H, H$_6$, J=~8.5 Hz), 6.57 (s, 1H, H$_3$), 7.19 (d, 2H, H$_\alpha$, J=8.5 Hz), 7.23 (d, 1H, H$_5$, J=~8.5 Hz), 7.61 (d, 2H, H$_\beta$, J=8.5 Hz).

The last crops were mixtures since the $^1$H nmr spectra (D$_2$O) revealed two slightly different methyls ($\delta$3.02 and 3.10), two different H$_6$'s ($\delta$5.67 and 5.75, both doublets, J=~8.5 Hz) and a complex multiplet from $\delta$7.2-8.2 other than the simple AB pattern of the above para-sulfonated compounds. These fractions fluoresced in water at 477–480 nm (excited 390 nm) and 475–477 nm in 50% aqueous ethanol.

The coumarins and azacoumarins prepared in the foregoing examples are water soluble and tests have shown that water solutions of them will lase.

What is claimed is:

1. A compound having the structure:

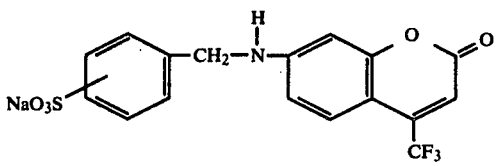

2. A compound having the structure:

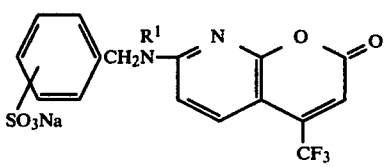

wherein R$^1$ is selected from the group consisting of H and CH$_3$.

* * * * *